United States Patent
Oka et al.

(10) Patent No.: US 11,826,094 B2
(45) Date of Patent: Nov. 28, 2023

(54) METHOD OF MANUFACTURING CATHETER AND CATHETER MANUFACTURED BY THE METHOD

(71) Applicant: Toray Industries, Inc., Tokyo (JP)

(72) Inventors: Yumi Oka, Otsu (JP); Kohei Fujii, Otsu (JP); Kota Tsukamoto, Otsu (JP)

(73) Assignee: Toray Industries, Inc., Tokyo (JP)

( * ) Notice: Subject to any disclaimer, the term of this patent is extended or adjusted under 35 U.S.C. 154(b) by 130 days.

(21) Appl. No.: 17/440,864

(22) PCT Filed: Mar. 27, 2020

(86) PCT No.: PCT/JP2020/013954
§ 371 (c)(1),
(2) Date: Sep. 20, 2021

(87) PCT Pub. No.: WO2020/203740
PCT Pub. Date: Oct. 8, 2020

(65) Prior Publication Data
US 2022/0160422 A1    May 26, 2022

(30) Foreign Application Priority Data
Mar. 29, 2019    (JP) .................. 2019-067552

(51) Int. Cl.
*A61B 18/14*    (2006.01)
*A61M 25/00*    (2006.01)
(Continued)

(52) U.S. Cl.
CPC ....... *A61B 18/1492* (2013.01); *A61M 25/001* (2013.01); *A61M 25/0009* (2013.01);
(Continued)

(58) Field of Classification Search
CPC ........... A61B 2017/00526; A61B 2018/00577; A61B 18/1492; A61M 25/0009;
(Continued)

(56) References Cited

U.S. PATENT DOCUMENTS 3,600,548 A * 8/1971 Bock .................. B23K 11/0046
                                                          219/79
4,239,953 A * 12/1980 Bock ...................... B23K 11/31
                                                          219/79
(Continued)

FOREIGN PATENT DOCUMENTS

JP    H10-510731 A    10/1998
JP    2004-065529 A    3/2004
(Continued)

OTHER PUBLICATIONS

Extended European Search Report dated Nov. 15, 2022, of counterpart European Patent Application No. 20783390.6.

*Primary Examiner* — Matthew P Travers
(74) *Attorney, Agent, or Firm* — DLA Piper LLP (US)

(57) ABSTRACT

A method of producing a catheter includes a step of arranging a lead wire in the lumen of a thermoplastic outer-layer tube such that the lead wire extends in the longitudinal direction of the outer-layer tube; a step of exposing one end of the lead wire out of an opening of the outer-layer tube; a step of joining the one end of the lead wire exposed out of the opening with the inner wall of a ring electrode; a step of covering the opening of the outer-layer tube with the ring electrode; an step of inserting a thermoplastic inner-layer tube in the lumen of the outer-layer tube; and an integrating step of heating the outer-layer tube and the inner-layer tube to integrate the outer-layer and the inner-layer tubes to form an electrode tip such that the lead wire is interlaminarly embedded and fixed between the outer-layer and the inner-layer tubes.

5 Claims, 4 Drawing Sheets

(51) Int. Cl.
*B29L 31/00* (2006.01)
*A61B 17/00* (2006.01)
*A61B 18/00* (2006.01)

(52) U.S. Cl.
CPC .............. *A61M 25/0012* (2013.01); *A61B 2017/00526* (2013.01); *A61B 2018/00577* (2013.01); *B29L 2031/7542* (2013.01)

(58) Field of Classification Search
CPC ............ A61M 25/001; A61M 25/0012; A61M 25/0015; B29L 2031/7542; B23K 11/002; B23K 11/0046
See application file for complete search history.

(56) References Cited

U.S. PATENT DOCUMENTS

| | | | | |
|---|---|---|---|---|
| 4,761,532 | A * | 8/1988 | Bock | B23K 11/0033 219/79 |
| 5,417,208 | A * | 5/1995 | Winkler | A61N 1/056 607/116 |
| 5,524,337 | A * | 6/1996 | Houser | B29C 66/91231 174/DIG. 8 |
| 5,545,149 | A * | 8/1996 | Brin | B29C 66/8264 604/525 |
| 5,555,618 | A | 9/1996 | Winkler | |
| 5,788,692 | A * | 8/1998 | Campbell | A61B 18/1815 606/41 |
| 6,030,371 | A * | 2/2000 | Pursley | A61M 25/0009 427/2.12 |
| 6,464,684 | B1 * | 10/2002 | Galdonik | A61M 25/005 604/527 |
| 7,993,481 | B2 * | 8/2011 | Hastings | A61B 5/287 604/524 |
| 10,668,275 | B2 * | 6/2020 | Anderson | A61N 1/056 |
| 2013/0079614 | A1 | 3/2013 | Harada et al. | |
| 2017/0354798 | A1 * | 12/2017 | Ogle | A61M 25/0043 |

FOREIGN PATENT DOCUMENTS

| | | |
|---|---|---|
| JP | 2009-268696 A | 11/2009 |
| JP | 2012-192005 A | 10/2012 |
| JP | 2013-533065 A | 8/2013 |
| JP | 2015-116309 A | 6/2015 |
| WO | 2008/115665 A1 | 9/2008 |
| WO | 2011/155424 A1 | 12/2011 |
| WO | 2012/019225 A1 | 2/2012 |
| WO | 2012/074580 A1 | 6/2012 |
| WO | 2019/055635 A1 | 3/2019 |

* cited by examiner

METHOD OF MANUFACTURING CATHETER AND CATHETER MANUFACTURED BY THE METHOD

TECHNICAL FIELD

This disclosure relates to a method of producing a catheter having an electrode tip at the front end of the catheter, and to a catheter produced using the method.

BACKGROUND

Catheter ablation is a method of treating arrhythmia, in which method, an ablation catheter is inserted in the heart chamber, and the cardiac muscle tissue is cauterized with an electrode attached to the distal end side of the catheter. In recent years, there has been development of such an ablation catheter with a balloon as cauterizes the cardiac muscle tissue such that the balloon attached to the distal end side of the catheter is transcutaneously introduced into the inferior vena cava, brought from the right atrium of the heart up to the left atrium via the atrial septum, inflated in the left atrium, and heated with a high-frequency current applied to an electrode inside the balloon.

In respect of treatment with use of an ablation catheter with a balloon, WO 2011/155424 discloses an ablation catheter with a balloon, in which the ablation catheter additionally has an electrophysiological examination function to verify the determination of a cauterization site and the treatment effect.

There is a widely known method in which a temperature measurement electrode is fixed at the front end of a catheter, and lead wires joined with the measurement electrode are wired to the proximal end. A known method of decreasing the risk of breakage of many lead wires wired to the measurement electrode includes use of a catheter with an electrode, the catheter having different lead wires inserted and wired in different lumens. In respect of this catheter with an electrode, JP 2009-268696 A discloses a method of fixing the electrode, in which method an adhesive is applied to the inner periphery of the measurement electrode, which is thus fixed at or around the distal end of the catheter.

In addition, another method is disclosed (JP 2013-533065 A), in which method lead wires are wound in spiral form, and arranged between the layers of a multilayered tube.

However, such a method that involves the attachment of a measurement electrode to the front end of a catheter as described in WO '424 and JP '696 is not sufficient to decrease the risk related to the disconnection of the connection portion between the measurement electrode and one end of the lead wire, thus posing the possibility of occurrence of a problem, for example, in that the adhesive is protruded or insufficient.

Another method involves arranging the lead wires of a measurement electrode such that the lead wires are spirally wound around a tube, and that the outside of the resulting piece is further covered with lead wires. Such a method poses a problem in that the production method is complicated, and a problem with insulation between the plurality of lead wires.

In view of this, there is a need to provide the following: a method of producing a catheter that makes it possible to decrease the risk of detachment of the lead wires from the electrode and the risk of breakage of the lead wires; and a catheter produced using the method.

SUMMARY

We thus provide (1) to (7):
(1) A method of producing a catheter, including: an arranging step (1) of arranging a lead wire in the lumen of a thermoplastic outer-layer tube such that the lead wire extends in the longitudinal direction of the outer-layer tube; an exposing step of exposing one end of the lead wire out of an opening of the outer-layer tube; a joining step (1) of electrically joining the one end of the lead wire exposed out of the opening with the inner wall of a ring electrode; a covering step of covering the opening of the outer-layer tube with the ring electrode; an inserting step of inserting a thermoplastic inner-layer tube in the lumen of the outer-layer tube; and an integrating step of heating the outer-layer tube and the inner-layer tube to integrate the outer-layer tube and the inner-layer tube to form an electrode tip such that the lead wire is interlaminarly embedded and fixed between the outer-layer tube and the inner-layer tube.
(2) The producing method according to (1), further including: an arranging step (2) of arranging a second lead wire in the lumen of the outer-layer tube such that the second lead wire extends in the longitudinal direction of the outer-layer tube, and is not in contact with the first lead wire; and a joining step (2) of joining one end of the second lead wire exposed out of the opening with the inner wall of a second ring electrode.
(3) The producing method according to (1) or (2), wherein, in the integrating step, the outer-layer tube is covered with a heat-shrinkable tube, and heated while a compression load is applied between the front end side and back end side of the inner-layer tube to form the electrode tip.
(4) The producing method according to any one of (1) to (3), wherein, in the joining step, one resistance welding electrode is inserted into the lumen of the outer-layer tube, another resistance welding electrode is brought in contact with the outer wall of the ring electrode, and the ring electrode and the lead wire are pressed between the resistance welding electrodes, and thus welded.
(5) The producing method according to any one of (1) to (4), including; an arranging step (3) of arranging, inside the outer-layer tube, a tubular member having an opening, and sandwiching the lead wire between the outer-layer tube and the tubular member; and a locating step of locating a position such that the opening of the outer-layer tube overlaps the opening of the tubular member.
(6) The producing method according to (5), wherein, in the joining step, one end of the lead wire and the inner wall of the ring electrode are joined, wherein the one end is exposed out of an opening formed with the opening of the outer-layer tube and the opening of the tubular member that are overlapped by each other in the locating step.
(7) A catheter produced by the producing method according to any one of (1) to (6).

In addition, we provide (8) to (12):
(8) A method of producing a catheter, including: an arranging step (1) of arranging a lead wire in the lumen of a thermoplastic outer-layer tube such that the lead wire extends in the longitudinal direction of the outer-layer tube; an exposing step of exposing one end of the lead wire out of an opening of the outer-layer tube; a joining step (1) of electrically joining the one end of the lead wire exposed out of the opening with the inner wall of a ring electrode; a covering step of covering the opening of the outer-layer tube with the ring electrode; an inserting step of inserting a thermoplastic inner-layer tube in the lumen of the outer-layer tube; and an integrating step of heating the outer-layer tube and the inner-layer tube to integrate the outer-layer tube and the inner-layer tube to form an electrode tip such that the lead wire is interlaminarly embedded and fixed between the outer-layer tube and the inner-layer tube.

(9) The producing method according to (8), further including: an arranging step (2) of arranging a second lead wire in the lumen of the outer-layer tube such that the second lead wire extends in the longitudinal direction of the outer-layer tube, and is not in contact with the first lead wire; and a joining step (2) of joining one end of the second lead wire exposed out of the opening with the inner wall of a second ring electrode.

(10) The producing method according to (8) or (9), wherein, in the integrating step, the outer-layer tube is covered with a heat-shrinkable tube, and heated while a compression load is applied between the front end side and back end side of the inner-layer tube to form the electrode tip.

(11) The producing method according to any one of (8) to (10), wherein, in the joining step, one resistance welding electrode is inserted into the lumen of the outer-layer tube, another resistance welding electrode is brought in contact with the outer wall of the ring electrode, and the ring electrode and the lead wire are pressed between the resistance welding electrodes, and thus welded.

(12) A catheter produced by the producing method according to any one of (8) to (11).

According to our method of producing a catheter, thermoplastic tubes are integrated such that a lead wire joined with the inner wall of a ring electrode is embedded between the tubes forming an electrode tip, thus making it possible to obtain a catheter that makes it possible to decrease the risk of detachment of the electrode from the lead wire and the risk of breakage of the lead wire.

Figure 1:
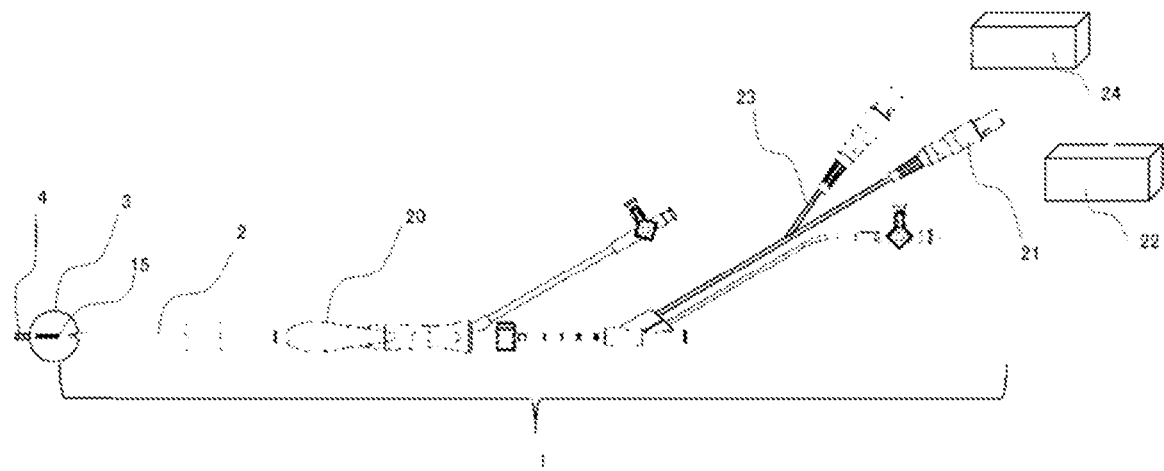
FIG. 1 is a schematic view depicting a catheter produced by the producing method according to an example.

REFERENCE SIGNS LIST 1 catheter
2 catheter shaft
3 balloon
4 electrode tip
10 tube
11 ring electrode
12 lead wire
13 inner shaft
14 outer shaft
15 high-frequency electrifying electrode
16 electrode temperature sensor
20 handle
21 connector
22 external electrophysiological examination device
23 connector
24 high-frequency generator
30 outer-layer tube
31 inner-layer tube
32 opening
33 core wire
34 compression spring
35 heat-shrinkable tube
36 laserbeam
37 fixing jig
42 one electric resistance welding electrode
43 another electric resistance welding electrode
50 tubular member
51 opening of tubular member

DETAILED DESCRIPTION

Below, preferred examples will be described in detail with reference to the drawings, but our methods and catheters are not limited to these aspects. In this regard, like reference signs refer to like elements, and the duplication of the same description is omitted. In addition, the ratios in the drawing do not necessarily accord with the description.

Our method of producing a catheter is characterized by including: an arranging step (1) of arranging a lead wire in the lumen of a thermoplastic outer-layer tube such that the lead wire extends in the longitudinal direction of the outer-layer tube; an exposing step of exposing one end of the lead wire out of an opening of the outer-layer tube; a joining step (1) of electrically joining the one end of the lead wire exposed out of the opening with the inner wall of a ring electrode; a covering step of covering the opening of the outer-layer tube with the ring electrode; an inserting step of inserting a thermoplastic inner-layer tube in the lumen of the outer-layer tube; and an integrating step of heating the outer-layer tube and the inner-layer tube to integrate the outer-layer tube and the inner-layer tube to form an electrode tip such that the lead wire is interlaminarly embedded and fixed between the outer-layer tube and the inner-layer tube.

The back end side refers to the proximal side in the longitudinal direction of the catheter, and the front end side refers to the distal side in the longitudinal direction of the catheter.

FIG. 1 illustrates a schematic view depicting a catheter having an electrode tip at the front end thereof and produced by our method.

In FIG. 1, a catheter 1 includes the following: a catheter shaft 2; and a balloon 3 and an electrode tip 4 that are arranged on the distal end side of the catheter shaft. The electrode tip 4 includes a tube 10, a ring electrode 11, and a lead wire 12 connected to the ring electrode 11.

The electrode tip 4 is arranged at and around the front end side of the catheter shaft 2, and the lead wire connected to the ring electrode extends toward the proximal side of the catheter shaft. The catheter shaft 2 is constituted of an inner shaft 13 and an outer shaft 14. Examples of materials of the inner shaft 13 and the outer shaft 14 include, but are not limited to, fluorine polymers, polyamides, polyurethane polymers, polyimides and the like. The inner shaft 13 extends through the inside of the balloon 3 up to the distal end of the catheter 1.

The inside of the balloon 3 includes a high-frequency electrifying electrode 15 and an electrode temperature sensor 16. The high-frequency electrifying electrode 15 is arranged to be wound around the outer wall of the inner shaft 13. The lead wire 6 enters between the high-frequency electrifying electrode 15 and the inner shaft 13 inside the balloon 3, and is wired toward the back end side of the catheter 1.

For example, when the ring electrode 11 is used to map cardiac potential, the electrode tip 4 including a plurality of ring electrodes 11 makes it possible to measure the shape of the potential accurately.

The proximal side of the catheter shaft 2 is provided with a handle 20, a connector 21, an external electrophysiological examination device 22, a connector 23, and a high-frequency generator 24, and the end of the lead wire 12 can be connected to the external electrophysiological examination device 22 via the connector 21. Additionally, when the ring electrode 11 is used as an RF electrode, the ring electrode can be connected to a high-frequency generator.

Figure 2:
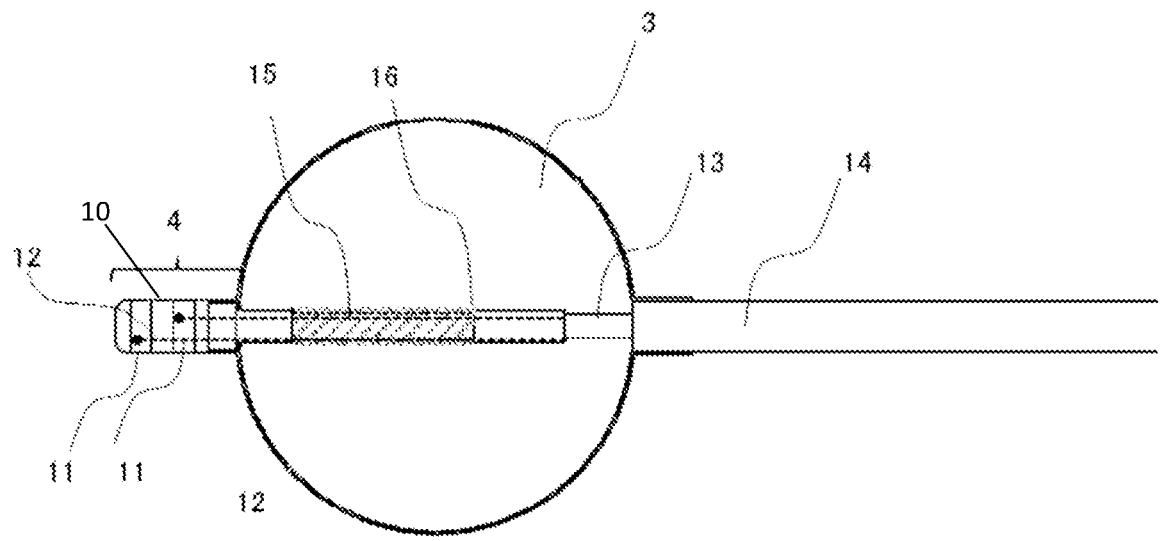
FIG. 2 is a schematic view of an electrode tip in the producing method according to an example.

FIG. 2 illustrates a schematic view of an electrode tip 4 in our method.

Electrode Tip

The electrode tip 4 includes a tube 10, a ring electrode 11, and a lead wire 12 connected to the ring electrode 11. To the inner wall of the tube 10, the inner shaft of the catheter shaft is adhered. On the outer wall of the electrode tip, a ring electrode is arranged.

For good access to the inside of an atrium, the tube 10 preferably has an outer diameter of 1 mm to 6 mm. The material to be used for the tube 10 is a thermoplastic resin, more preferably polyurethane or the like, from the viewpoint of hardness in light of the safety of the operation inside an atrium.

Ring Electrode

The end of the lead wire 12 is joined with the inner wall of the ring electrode 11, the lead wire 12 extends in an embedded manner in the tube 10, and the lead wire 12 is protruded from the proximal end of the ring electrode 11, and wired into the lumen of the catheter shaft 2.

The electrode tip 4 may have two or more ring electrodes 11. The ring electrodes 11 arranged on the electrode tip 4 are not limited to any particular number, provided that the ring electrodes 11 as well as the lead wires 12 connected to the respective ring electrodes 11 are arranged to not be in electrical contact with each other.

When a plurality of ring electrodes 11 are arranged on the electrode tip 4, the ring electrodes 11 are preferably arranged with a space of 0.5 mm to 3.0 mm between them.

To prevent contact during production, the lead wires 12 connected with the respective ring electrode 11 are preferably each arranged such that the lead wires 12 are located the most apart from each other during formation of the tube 10. For example, when the electrode tip 4 has two ring electrodes 11, the lead wires 12 are joined with the respective ring electrodes 11 to be opposed to each other 180° around the central axis of the tube 10, and embedded inside the tube 10.

To decrease the risk of wire breakage, the lead wire 12 and the ring electrode 11 are preferably joined in a fixed manner using a method such as welding or soldering. When welding is used, resistance welding and laser welding are preferable.

This electrode tip 4 can be used to treat, for example, arrhythmia such as atrial fibrillation, and thus, can be attached to the front end of the catheter. Examples of catheters for which the electrode tip is used include balloon catheters, ablation catheters, ablation catheters with a balloon and the like, and the electrode tip is preferably used for an ablation catheter with a balloon.

Lead Wire

The lead wire 12 is not limited to any particular diameter, and the lead wire 12 preferably has a diameter of 0.05 mm to 0.30 mm from the viewpoint of decreasing the risk of wire breakage during wiring and from the viewpoint of making it easy to secure a space for wiring to the electrode tip or the catheter shaft portion.

A material to be preferably used for the lead wire is phosphor bronze, copper or the like. In addition, a material to be preferably used for the ring electrode is platinum, stainless steel, gold, silver, copper, an alloy thereof or the like, considering contact with an organism.

Figure 3:
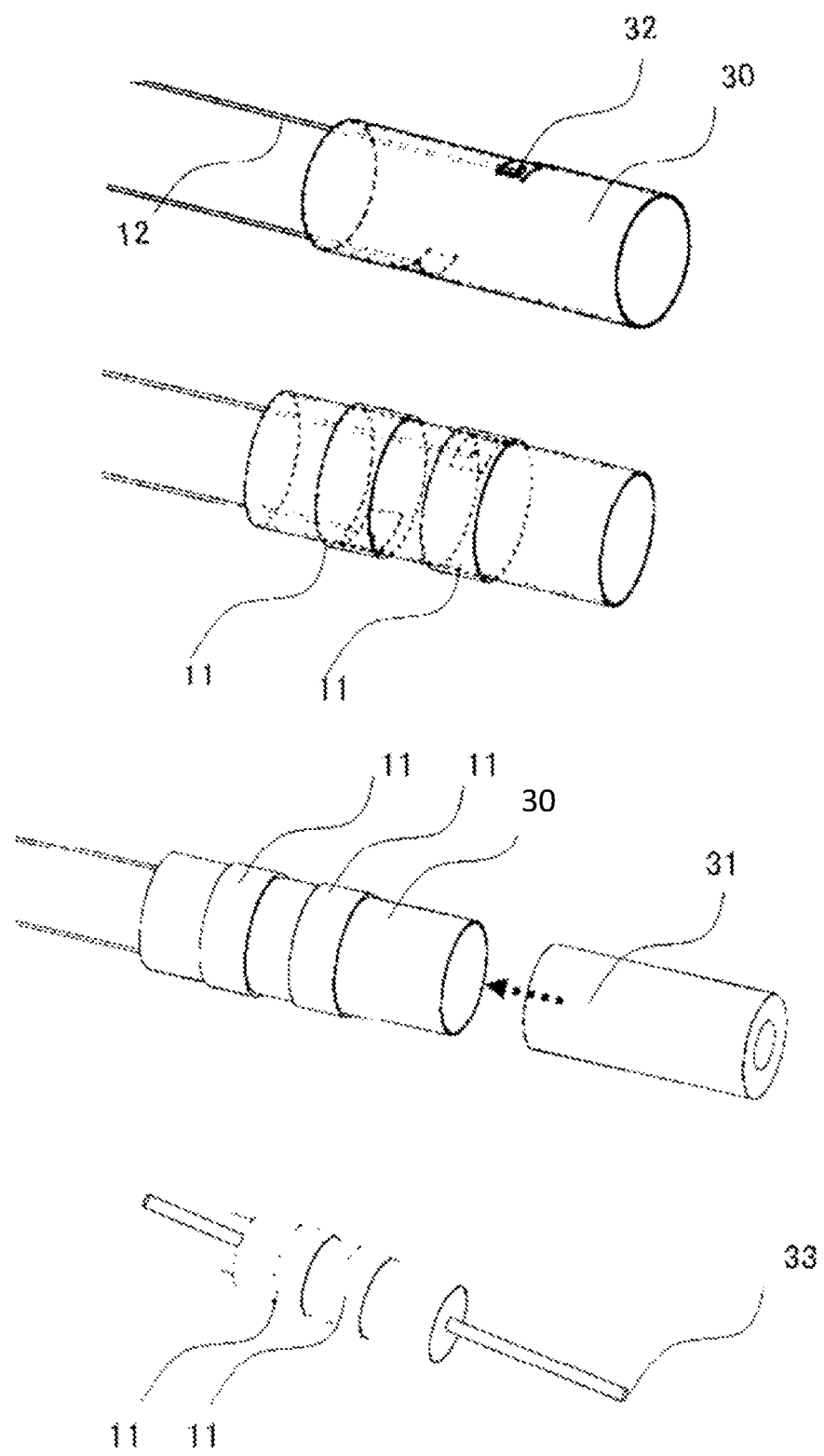
FIG. 3 is a schematic diagram depicting a series of processes in our method.

FIG. 3 illustrates a schematic diagram of a series of processes in a method of producing an electrode tip in a catheter having an electrode tip according to an example.

Arranging Step of Arranging Lead Wire in Lumen of Thermoplastic Outer-Layer Tube Such that Lead Wire Extends in Longitudinal Direction of Outer-Layer Tube An outer-layer tube 30 containing a thermoplastic resin and a lead wire 12 are provided. The lead wire 12 is arranged in the lumen of the thermoplastic outer-layer tube 30 such that the lead wire extends in parallel with the longitudinal direction of the outer-layer tube 30. In this example, the lead wire 12 extending in parallel with the longitudinal direction in the lumen of the outer-layer tube 30 does not need to be strictly parallel with respect to the longitudinal direction of the outer-layer tube 30.

Specifically, this means that the lead wire 12 is not wound but is extended from the distal end of the outer-layer tube 30 toward the proximal end, and this meaning encompasses examples where the lead wire 12 is slightly loosened or sagged, and thus is not strictly parallelized.

Exposing Step of Exposing One End of Lead Wire Out of Opening of Outer-Layer Tube Next, an opening 32 is formed in the outer wall of the outer-layer tube 30, out of which opening, the lead wire 12 stripped of an insulating coating is exposed. The opening 32 may have an arbitrary size, but should have a size that can be covered with the ring electrode 11.

When a plurality of ring electrodes 11 are arranged in the electrode tip 4, the corresponding plurality of lead wires 12 are arranged, and thus, the openings 32 the number of which corresponds to that of the lead wires 12 are formed in the outer-layer tube 30. In addition, the openings 32 are formed at the positions spaced from each other in the longitudinal direction of the outer-layer tube 30 to expose the lead wires 12 at the respective positions of the ring electrodes 11 corresponding to the openings.

Joining Step of Electrically Joining One End of Lead Wire Exposed out of Opening with Inner Wall of Ring Electrode Next, one end of the lead wire 12 and the inner wall of the ring electrode are electrically joined using a method such as welding or soldering. The electrical joining is performed such that the one end of the lead wire 12 comes in contact with the inner wall of the ring electrode 11.

The electrical joining refers to joining the lead wire and the ring electrode so that electricity can be conducted between the lead wire and the ring electrode.

FIG. 3 illustrates an example of a joining step.

The lead wire 12 is extended in parallel with the longitudinal direction of the outer-layer tube 30 in the lumen of the outer-layer tube 30, and the outer-layer tube 30 is covered with the ring electrode 11. Next, one electric resistance welding electrode 42 is inserted into the lumen of the outer-layer tube 30, and the lead wire 12 and the electric resistance welding electrode 42 are brought in contact with each other. The lead wire 12 is exposed through the opening 32 out of the outer-layer tube 30. The one end of the lead wire 12 exposed is brought in contact with the inner wall of the ring electrode 11.

Another resistance welding electrode 43 is brought in contact with the outer wall of the ring electrode 11. The ring electrode 11 and the lead wire 12 are pressed between the electrodes, and electrically joined by welding.

The resistance welding electrode is not limited to a particular material, and a material to be used is copper, chromium copper, tungsten or the like. It is preferable that the shape of the front end of the one resistance welding electrode 42 is smaller than the opening 32, and is shaped to conform to the inner diametric shape of the tube so that the lead wire 12 can be exposed out of the outer-layer tube 30 to be brought in contact with the inner wall of the ring electrode 11. For example, the shape is preferably arc-shaped if the outer-layer tube 30 is cylindrical.

This method makes it possible that the lead wire 12 is electrically joined with the inner wall of the ring electrode 11 in a reliable manner and in a short time. That method also makes it possible that the ring electrode 11 and the lead wire 12 are electrically joined without changing the state where the opening 32 of the outer-layer tube 30 is covered with the ring electrode 11. This involves neither unnecessarily drawing the lead wire 12 out nor drawing the lead wire back, accordingly makes it possible to decrease the risk of wire breakage, and thus, is preferable, compared to a conventional method in which the lead wire 12 is much drawn out of the opening 32, and electrically joined with the inner wall of the ring electrode 11, and the excessive portion of the lead wire 12 is drawn back through the opening while the outer-layer tube 30 is covered with the ring electrode 11.

Covering Step of Covering Opening of Outer-Layer Tube with Ring Electrode

The ring electrode 11 is caused to cover the outer-layer tube 30 to cover the opening 32. The ring electrode is allowed to cover the opening before being electrically joined with the lead wire as above-mentioned, and then be electrically joined at the position of covering, or may be electrically joined at a position deviated from the opening, followed by covering the opening with the ring electrode. Thus, arranging the ring electrode 11 at the position at which to cover the opening 32 of the outer-layer tube 30 makes it possible to prevent the lead wire 12 from being exposed to the outside.

Inserting Step of Inserting Inner-Layer Tube in Lumen of Outer-Layer Tube

An inner-layer tube 31 containing a thermoplastic resin is provided, and the inner-layer tube 31 is inserted into the lumen of the outer-layer tube 30. When this is done, the inner-layer tube 31 is inserted such that the lead wire 12 is inserted interlaminarly between the outer-layer tube 30 and the inner-layer tube 31, maintaining the arrangement form extended in the longitudinal direction of the tubes. The inner diameter of the outer-layer tube 30 is larger than the outer diameter of the inner-layer tube 31, and thus, the inner-layer tube 31 can be inserted into the lumen of the outer-layer tube 30. In this regard, the step of inserting the inner-layer tube 31 into the lumen of the outer-layer tube 30 may be followed by a step of arranging the lead wire 12 in the lumen of the outer-layer tube 30 to extend in the longitudinal direction of the outer-layer tube 30. In this example, the lead wire 12 is arranged in the lumen of the outer-layer tube 30 such that the lead wire 12 is inserted interlaminarly between the outer-layer tube 30 and the inner-layer tube 31.

Allowing the lead wire 12 to be arranged to extend in parallel with the longitudinal direction interlaminarly between the outer-layer tube 30 and the inner-layer tube 31 makes it possible to inhibit a load from being applied in the direction in which the lead wire 12 is separated from the ring electrode 11, and thus to decrease the risk of wire breakage of the lead wire 12 and the electrically joined portion between the lead wire 12 and the ring electrode 11. Additionally, when two or more lead wires 12 are used, arranging the lead wires as above-mentioned makes it possible to decrease the risk of intertanglement and contact between the lead wires.

Integrating Step of Heating Outer-Layer Tube and Inner-Layer Tube to Integrate Outer-Layer Tube and Inner-Layer Tube Such that Lead Wire is Interlaminarly Embedded and Fixed Between Outer-Layer Tube and Inner-Layer Tube A core wire 33 for heating the outer-layer tube 30 and the inner-layer tube 31 is inserted into the lumen of the inner-layer tube 31.

The outer-layer tube 30 and the inner-layer tube 31 contains a thermoplastic resin, and thus, heating the core wire 33 causes the outer-layer tube 30 and the inner-layer tube 31 to be integrated to form a tube 10. The lead wire 12 is arranged between the outer-layer tube 30 and the inner-layer tube 31, and thus, the lead wire 12 is interlaminarly embedded and fixed, extending in parallel with the longitudinal direction between the outer-layer tube 30 and the inner-layer tube 31. As a result, the lead wire 12 is embedded and fixed to extend in parallel with the inside of the tube 10, and the ring electrode 11 is fixed on the outer wall of the tube 10.

In the above-mentioned producing method, the outer-layer tube 30 and the inner-layer tube 31 are integrated to form the tube 10 with the lead wire 12 arranged to extend in parallel with and between the outer-layer tube 30 and the inner-layer tube 31, and thus, the lead wire 12 is fixed, extending in parallel with and inside the tube 10.

This makes it possible to inhibit a load from being applied to the electrically joined portion between the ring electrode 11 and the lead wire 12 even if the electrode tip 4 is curved during the operation of the catheter 1. In addition, the above-mentioned arrangement makes it less likely that the lead wire 12 is broken by twisting or moving, and thus, makes it possible to decrease the risk of wire breakage of the lead wire.

In addition, the insulating coating of the lead wire 12 is opened at and around the joined site between the ring electrode 11 and the lead wire 12, which are thus ready to be in electrical contact. When the electrode tip 4 includes a plurality of ring electrodes 11, this can pose the possibility that a plurality of lead wires 12 come in contact with each other during production, but, when the outer-layer tube 30 and the inner-layer tube 31 are integrated, the lead wires 12 are arranged to extend in parallel with each other, thus making it possible to prevent the lead wires 12 from coming in contact with each other, and to provide reliable insulation because the tube 10 is arranged between the lead wires 12.

The above-mentioned outer-layer tube 30, inner-layer tube 31, and tube 10 can be set to any thickness. In addition, the outer-layer tube 30 and the inner-layer tube 31 are preferably composed of the same thermoplastic resin because the integrally formed tube 10 can have stable strength.

Figure 4:
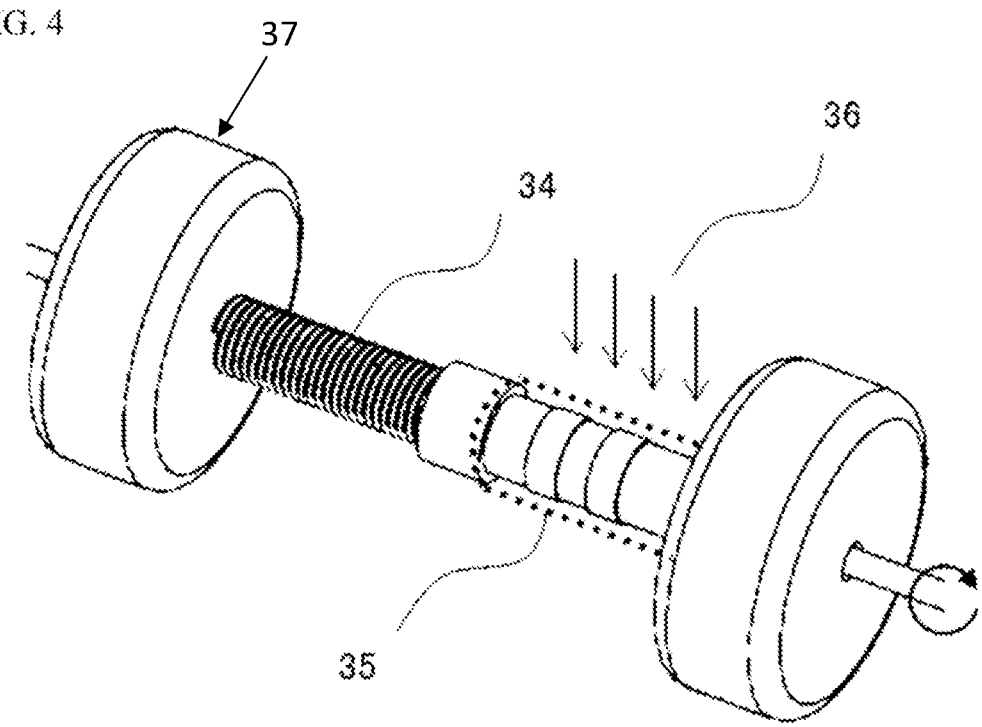
FIG. 4 illustrates an example of an integrating step in our method.

FIG. 4 illustrates a variant example of a step of heating the outer-layer tube 30 and the inner-layer tube 31 to integrate the outer-layer tube 30 and the inner-layer tube 31 such that the lead wire 12 is interlaminarly embedded and fixed between the outer-layer tube 30 and the inner-layer tube 31.

In the step of integrating the outer-layer tube 30 and the inner-layer tube 31, a compression load is applied between the front end side and back end side of the inner-layer tube 31. One end of the outer-layer tube 30 and inner-layer tube 31 is fixed with a fixing jig 37, a compression spring 34 is brought in contact with the other end, and the compression spring 34 is fixed with a fixing jig 37 at a position that causes compression. This makes it easy to apply a compression load and at the same time perform heating.

Next, the ring electrode 11 and the outer wall of the outer-layer tube 30 are covered with a heat-shrinkable tube 35. The heat-shrinkable tube 35 having the smallest shrinkage inner diameter smaller than the outer diameter of the ring electrode 11 can provide a sufficient shrinkage force, and thus, is preferable.

In addition, a core wire 33 is inserted into the lumen of the inner-layer tube 31. The core wire 33, which is made of metal such as stainless steel, is heated to be adhered to the inner-layer tube 31, and thus, preferably undergoes surface-treatment or the like to have good releasability.

Next, a heating procedure is performed. The source of heat is preferably a laserbeam 36. The laserbeam 36 is preferably a carbon dioxide gas laser or a semiconductor laser. Exposure to the laserbeam 36 with the core wire 33 being rotated makes it possible to uniformly heat the whole circumference of the outer-layer tube 30 and inner-layer tube 31 which are being integrated. In addition, simultaneously moving the exposure position of the laserbeam 36 makes it possible to continuously heat the outer-layer tube 30 and inner-layer tube 31 in the longitudinal direction.

Continuously heating the outer-layer tube 30 and the inner-layer tube 31 in the longitudinal direction makes it possible to prevent the lead wire 12 from deviating from the arrangement of extension in the longitudinal direction of the outer-layer tube 30 and inner-layer tube 31 which are being integrated. In addition, not only the ring electrode 11 is locally heated, but also the portions that are interlaminar between the outer-layer tube 30 and the inner-layer tube 31 and are not covered with the ring electrode 11 are heated, thus making it possible to decrease the risk of applying an unnecessary load to the lead wires 12, and to decrease the risk of short-circuit between the lead wires 12.

The compression spring 34 applying a compression load results in expanding the outer-layer tube 30 and the inner-layer tube 31 in the radial direction, and heating the ring electrode 11 and the outer-layer tube 30 which are covered with the heat-shrinkable tube 35 results in effectively filling up the gap between the ring electrode 11 and the outer-layer tube 30, thus obviating a difference in the level between the ring electrode 11 and the outer wall of the outer-layer tube 30. The heat-shrinkable tube 35 is not limited to any particular material, and an olefin resin material or a fluorine resin material is preferably used. The heat-shrinkable tube 35 is detached after the integration processing.

Figure 5:
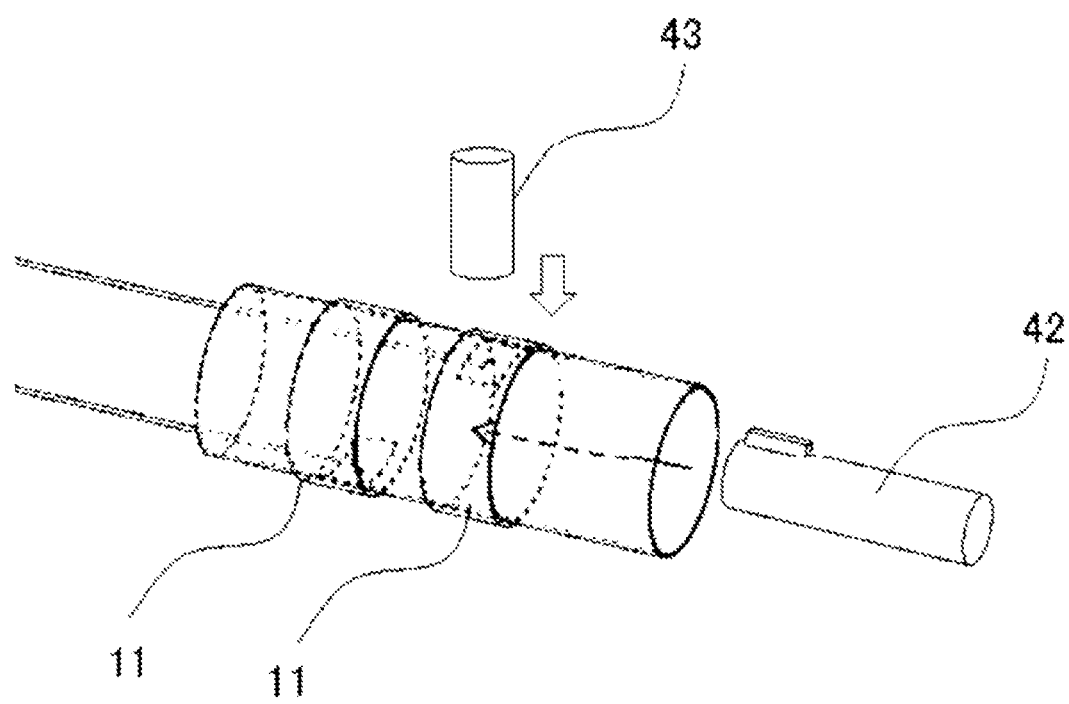
FIG. 5 illustrates an example of a joining step in our method.

FIG. 5 illustrates an example of a joining step.

The lead wire is extended in generally parallel with the longitudinal direction of the outer-layer tube in the lumen of the outer-layer tube such that the outer-layer tube is covered with the ring electrode. Next, one electric resistance welding electrode 42 is inserted into the lumen of the outer-layer tube, and brought in contact with the lead wire. The lead wire is protruded through an opening out of the outer periphery of the outer-layer tube, and the lead wire is brought in contact with the inner periphery of the ring-shaped electrode.

Another electric resistance welding electrode 43 is brought in contact with the outer periphery of the ring-shaped electrode, the parts between the welding electrodes are electrically joined by electric resistance welding while being pressed.

The resistance welding electrode is not limited to any particular material, and a material to be used is copper, chromium copper, tungsten or the like. The shape of the front end of the resistance welding electrode is preferably an arc-shaped surface smaller than the opening to enable the lead wire to protrude through the opening and be brought in contact with the inner periphery of the ring electrode.

Figure 6:
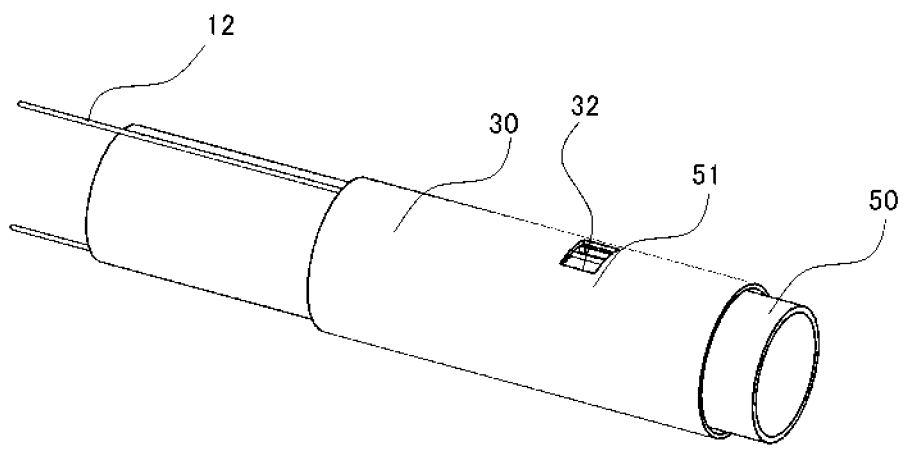
FIG. 6 illustrates an example of an arranging step and a locating step which involve using a tubular member in our method.

FIG. 6 illustrates an example of an arranging step and a locating step which involve using a tubular member.

Arranging Step of Arranging, Inside Outer-Layer Tube, Tubular Member Having Opening, and Sandwiching Lead Wire Between Outer-Layer Tube and Tubular Member To prevent each arranging step from taking a long time, a tubular member 50 having an opening 51 is provided, and the tubular member 50 is further arranged inside from the lead wire 12 arranged to extend in parallel with the longitudinal direction in the lumen of the above-mentioned outer-layer tube 30. Thus, both arranging, inside the outer-layer tube 30, the tubular member 50 having the opening 51, and sandwiching the lead wire 12 between the outer-layer tube 30 and the tubular member 50 allow the lead wire 12 and the outer-layer tube 30 to be supported by the tubular member 50. To be supported means that the state where the outer-layer tube 30 and the lead wire 12 are arranged at the respective positions is maintained under no external force. Furthermore, even when an external force is applied to the outer-layer tube 30 and the lead wire 12 in the arranging steps (1) to (3), the tubular member 50 existing inside from the outer-layer tube 30 makes it possible that the shape of the outer-layer tube 30 is maintained, and that the position of the lead wire 12 is prevented from deviating.

Locating Step of Locating Position Such that Opening of Outer-Layer Tube Overlaps Opening of Tubular Member Next, the opening 32 of the outer-layer tube 30 and the opening 51 of the tubular member 50 are located to overlap. This makes it possible that, in the joining step of electrically joining one end of the lead wire exposed out of an opening with the inner wall of the ring electrode, the lead wire 12 is exposed out of the outer-layer tube 30 through the opening made by the overlapping of the opening of the outer-layer tube 30 and the opening 51 of the tubular member 50 when the one electric resistance welding electrode 42 is inserted into the lumen of the tubular member 50 and the outer-layer tube 30 to bring the lead wire 12 in contact with the electric resistance welding electrode 42. This makes it possible that the front end of the one electric resistance welding electrode 42 passes through the opening 51 to come in contact with the lead wire 12 without coming in contact with the tubular member 50. Then, the lead wire 12 can be protruded through the opening 32 out of the outer periphery of the outer-layer tube 30, and the lead wire can be brought in contact with the inner periphery of the ring-shaped electrode.

That is, a method of producing a catheter, including; an arranging step (3) of arranging, inside the outer-layer tube, a tubular member having an opening, and sandwiching the lead wire between the outer-layer tube and the tubular member; and a locating step of locating the position such that the opening of the outer-layer tube overlaps the opening of tubular member, is illustrated as one aspect of a method of producing a catheter. These arranging step (3) and locating step need only to be performed after the arranging step of arranging the lead wire in the lumen of the thermoplastic outer-layer tube to extend the lead wire in the longitudinal direction of the outer-layer tube, and before the exposing step of exposing one end of the lead wire out of the opening of the outer-layer tube.

The opening 51 of the tubular member 50 is not limited to any particular shape, and needs only to be formed such that the opening of the outer-layer tube 30 and the opening 51 of the tubular member 50 overlap when the tubular member 50 is arranged inside the outer-layer tube 30. The opening 51 preferably has the same shape as the opening 32 of the outer-layer tube 30.

The outer diameter of the tubular member 50 needs only to be in the range that makes it possible to sandwich the lead wire 12 between the outer-layer tube 30 and the tubular member 50, and further to support the lead wire and the outer-layer tube. The outer diameter R of the tubular member 50 is preferably in the range of $0.9 \times r \leq R \leq 1.1 \times r$, wherein the inner diameter of the outer-layer tube is D1, the diameter of the lead wire 12 is D2, and $D1-(D2 \times 2)=r$.

In addition, the inner diameter of the tubular member 50 is not limited to any particular value, and needs only to be such that the one electric resistance welding electrode 42 does not come in contact with the tubular member 50 when the one electric resistance welding electrode one 42 is inserted into the lumen of the tubular member 50 in the joining step.

The tubular member 50 is not limited to any particular material, and is preferably made of metal or resin from the viewpoint of ease of production and ease of handling. In addition, it is more preferable that the material is insulating to eliminate the possibility that electricity runs in the tubular member 50 to generate a welding defect during electric resistance welding in the joining step. Furthermore, even when the material is non-insulating, the material needs only to be electrically independent.

Using this method makes it possible to electrically join the lead wire with the inner periphery of the ring electrode in a reliable manner and in a short time, and makes it possible to electrically join the ring electrode with the lead wire with the outer-layer tube covered with the ring electrode. This involves neither unnecessarily drawing the lead wire out nor drawing the lead wire back, accordingly makes it possible to decrease the risk of wire breakage, and thus, is preferable, compared with a conventional method in which the lead wire is much drawn out of the opening, and electrically joined with the inner periphery of the ring electrode, and the excessive portion of the lead wire is drawn back through the opening while the outer-layer tube is covered with the ring electrode. In addition, electrical joining with an adhesive makes it difficult for the adhesive to effectively fill up a gap generated between the inner periphery of the ring electrode and the opening, and is complicated from the viewpoint of management of a leaky or insufficient adhesive. Accordingly, the above-mentioned method is preferable.

EXAMPLES

Example 1

A medical tubing device was used to produce a polyurethane-made outer-layer tube having an outer diameter of 3.6 mm, an inner diameter of 3.4 mm, and a length of 10 mm. In this outer-layer tube, two openings were made, each having a length of 0.9 mm in the longitudinal direction of the tube and a width of 1.2 mm. The first opening was formed at a position 3.5 mm apart from an end of the outer-layer tube, and the second opening was formed at a position that is 180° opposed to the first opening in the outer wall of the outer-layer tube, and is apart from 6.5 mm from the end of the outer-layer tube.

In addition, one end of a phosphor bronze wire covered with an insulating polyurethane coating and having a diameter of 0.1 mm was stripped of the insulating coating, and inserted into the lumen of the outer-layer tube.

The phosphor bronze wire stripped of the insulating coating was exposed out the opening of the outer-layer tube, and the phosphor bronze wire was extended in parallel with the longitudinal direction of the outer-layer tube.

Next, the outer-layer tube was covered with a platiniridium-made ring electrode having an outer diameter of 3.8 mm, an inner diameter of 3.6 mm, and a width of 1.5 mm such that the ring electrode was arranged at a position at which to cover the opening.

Next, a chromium-copper-made electric resistance welding electrode the front end of which was 0.5 mm square was inserted into the lumen of the outer-layer tube, and brought in contact with the lead wire. A chromium-copper-made resistance welding electrode the width of which was 1.5 mm and the front end of which had a semi-circular arc shape conforming to the circular arc shape of the ring electrode was brought in contact with the outer wall of the ring electrode. The parts between the electrodes were electrified under a pressure of 15 N to be thus joined by resistance welding.

Next, an inner-layer tube made of the same material as the outer-layer tube and having an outer diameter of 3.4 mm, an inner diameter of 1.7 mm, and a length of 15 mm was inserted into the lumen of the outer-layer tube, and a phosphor bronze wire was inserted interlaminarly between the outer-layer tube and the inner-layer tube and extended in the longitudinal direction. When this was done, the two phosphor bronze wires were arranged to be 180° opposed to each other between the layers.

The multilayered tube made in this manner was covered with a fluorine resin-made heat-shrinkable tube having an inner diameter of 4.5 mm before shrinkage, a thickness of 0.2 mm after shrinkage, and a length of 10 mm.

Furthermore, a stainless steel-made core member was inserted into the lumen of the inner-layer tube, one end of the inner-layer tube was fixed, a compression coil spring having a spring constant of 1 N/mm was attached to the other end, and a compression load of 10 N was applied between the front end side and back end side of the inner-layer tube.

Using a laser welding machine configured for a wavelength of 940 nm, the tube was rotated under a compression load and, at the same time, exposed to a laserbeam being caused to shift in the longitudinal direction of the tube.

The distal side of a polyamide-made inner shaft was inserted and adhered in the lumen of the electrode tip made in this manner, and the phosphor bronze wire connected to the ring electrode was wired toward the proximal side of this inner shaft.

Next, a copper wire a part of which was stripped of an insulating coating was provided as a high-frequency electrifying electrode, and a constantan-made sensor wire to be used as an electrode temperature sensor was provided. The copper wire was wound in coil form around the inner shaft such that both of these sandwiched the sensor wire therebetween. Thus, a coil-shaped high-frequency electrifying electrode having a length of 13 mm and the electrode temperature sensor arranged at the back end portion of the high-frequency electrifying electrode were formed. The copper wire and the sensor wire were wired toward the distal side along the inner shaft.

A polyurethane-made balloon was arranged to encompass the high-frequency electrifying electrode and the electrode temperature sensor that were formed in this manner. The distal end portion of the balloon was fixed to the electrode tip by heat welding, and the proximal end portion of the balloon was fixed to a polyurethane-made outer shaft by heat welding.

The proximal side of the catheter shaft had a handle, and the copper wire of the high-frequency electrifying electrode and the electrode temperature sensor wire were connected through the handle to a connector for a high-frequency generator.

In addition, the phosphor bronze wire connected to the ring electrode was also connected through the handle to a connector for measurement of electrical potential. Thus, a balloon catheter having the electrode tip in the Example was produced.

Example 2

Two openings each having a length of 0.9 mm in the longitudinal direction and a width of 1.2 mm were formed in a stainless steel tubular member having an outer diameter of 3.3 mm, an inner diameter of 2.6 mm, and a length of 12 mm such that the openings were formed to overlap respective openings of the outer-layer tube 30. The tubular member thus formed was arranged inside from the lead wire arranged to extend in parallel with the longitudinal direction of the lumen of the outer-layer tube. A balloon catheter having an electrode tip was produced in Example 2 under the same conditions as in Example 1 except these conditions.

Comparative Example

Using the ring electrode and the phosphor bronze wire that were described in Examples, the phosphor bronze wire stripped of an insulating coating was brought in contact with the inner wall of the ring electrode, and both of these were joined by resistance welding. A balloon catheter having an electrode tip was produced in Comparative Example in the same manner except that the outer-layer tube and the inner-layer tube which were described in Examples were not used, and that the lead wire was not embedded in the tube.
Verification of how Two Phosphor Bronze Wires are Embedded and Short-Circuited The electrode tip in each of the Examples was cut crosswise perpendicularly to the longitudinal direction. The resulting cross-section made it possible to verify that the phosphor bronze wires were embedded and fixed in the integrated multilayered tube, and that the two phosphor bronze wires were extended without contact with each other. In addition, a resistance measurement device was used to verify that both of them were not short-circuited.
Strength Test on Connected Portions of Phosphor Bronze Wires With the electrode tip in Example 1, the phosphor bronze wire and the polyurethane-made multilayered tube were pulled toward each other using a tensile tester at a testing speed of 10 mm/min to measure the breaking strength, with the result that the phosphor bronze wire was broken at 7.2 N at a wired position other than the welded portion.

With the electrode tip in Example 2, the phosphor bronze wire and the polyurethane-made multilayered tube were pulled toward each other using a tensile tester at a testing speed of 10 mm/min to measure the breaking strength, with the result that the phosphor bronze wire was broken at 7.5 N at a wired position other than the welded portion.

On the other hand, with the electrode tip in Comparative Example, the ring electrode and the phosphor bronze wire were pulled toward each other using a tensile tester at a testing speed of 10 mm/min to measure the breaking strength, with the result that the phosphor bronze wire was broken at 4.0 N at the welded portion.

The above-mentioned results have revealed that causing the phosphor bronze wire joined with the inner wall of the ring electrode to extend in an embedded manner in the tube in the electrode tip makes it possible to reinforce the fixation of the phosphor bronze wire and thus to obtain a catheter that decreases the risk of wire breakage.

INDUSTRIAL APPLICABILITY

Our methods and catheters can be used, in the field of medicine, as a catheter the front end of which has an electrode tip for treating, for example, arrhythmia such as atrial fibrillation.

The invention claimed is:

1. A method of producing a catheter, comprising:
an arranging step of arranging a lead wire in a lumen of a thermoplastic outer-layer tube such that said lead wire extends in a longitudinal direction of the outer-layer tube;
an exposing step of exposing one end of said lead wire out of an opening of said outer-layer tube;
a joining step of joining said one end of said lead wire exposed out of said opening with an inner wall of a ring electrode;
a covering step of covering said opening of said outer-layer tube with said ring electrode;
an inserting step of inserting a thermoplastic inner-layer tube in the lumen of said outer-layer tube; and
an integrating step of heating said outer-layer tube and the inner-layer tube to integrate said outer-layer tube and said inner-layer tube to form an electrode tip such that said lead wire is interlaminarly embedded and fixed between said outer-layer tube and said inner-layer tube,
wherein, in said integrating step, said outer-layer tube is covered with a heat-shrinkable tube, one end of the outer-layer tube and the inner-layer tube is fixed with a fixing jig, a compression spring is brought in contact with another end, and the outer-layer tube and the inner-layer tube are heated while a compression load is applied by the compression spring in the longitudinal direction between a front end side and a back end side of said inner-layer tube to form said electrode tip.

2. The method according to claim 1, further comprising:
another arranging step of arranging a second lead wire in the lumen of said outer-layer tube such that said second lead wire extends in the longitudinal direction of said outer-layer tube, and is not in contact with the first lead wire; and
another joining step of joining one end of said second lead wire exposed out of said opening with an inner wall of a second ring electrode.

3. The method according to claim 1, wherein, in said joining step, one resistance welding electrode is inserted into the lumen of said outer-layer tube, another resistance welding electrode is brought in contact with an outer wall of said ring electrode, and said ring electrode and said lead wire are pressed between said resistance welding electrodes, and thus welded.

4. The method according to claim 1, comprising:
a third arranging step of arranging, inside said outer-layer tube, a tubular member having an opening, and sandwiching said lead wire between said outer-layer tube and said tubular member; and a locating step of locating a position such that the opening of said outer-layer tube overlaps said opening of said tubular member.

5. The method according to claim 4, wherein, in said joining step, said one end of said lead wire and the inner wall of said ring electrode are joined, and the one end is exposed out of an opening formed with said opening of said outer-layer tube and said opening of said tubular member that are overlapped by each other in said locating step.

* * * * *